(12) United States Patent
DePhillipo et al.

(10) Patent No.: US 8,313,930 B2
(45) Date of Patent: *Nov. 20, 2012

(54) KITS AND METHODS FOR ASSESSING SKIN HEALTH

(75) Inventors: John R. DePhillipo, Margate, NJ (US); Robert P. Ricciardi, Glen Mills, PA (US)

(73) Assignee: Genelink, Inc., Margate, NY (US)

( * ) Notice: Subject to any disclaimer, the term of this patent is extended or adjusted under 35 U.S.C. 154(b) by 620 days.

This patent is subject to a terminal disclaimer.

(21) Appl. No.: 11/731,180

(22) Filed: Mar. 30, 2007

(65) Prior Publication Data

US 2007/0178518 A1 Aug. 2, 2007

Related U.S. Application Data

(60) Division of application No. 10/247,935, filed on Sep. 20, 2002, now Pat. No. 7,211,383, which is a continuation-in-part of application No. PCT/US02/10682, filed on Apr. 5, 2002, and a continuation-in-part of application No. 09/826,522, filed on Apr. 5, 2001, now abandoned.

(60) Provisional application No. 60/289,169, filed on May 7, 2001, provisional application No. 60/350,517, filed on Oct. 22, 2001, provisional application No. 60/335,426, filed on Oct. 24, 2001, provisional application No. 60/336,815, filed on Dec. 5, 2001.

(51) Int. Cl.
*C12P 19/34* (2006.01)
*C12Q 1/68* (2006.01)

(52) U.S. Cl. .......................... 435/91.2; 435/6.1

(58) Field of Classification Search .............. 435/91.2, 435/6.1
See application file for complete search history.

(56) References Cited

U.S. PATENT DOCUMENTS

| | | | |
|---|---|---|---|
| 4,757,063 A | 7/1988 | Parnham | 514/183 |
| 5,585,232 A | 12/1996 | Farr | 435/6 |
| 5,834,044 A | 11/1998 | Schmitz et al. | 426/73 |
| 5,891,622 A | 4/1999 | Morrow et al. | 435/4 |
| 5,950,634 A | 9/1999 | Ochi et al. | 128/898 |
| 5,955,111 A | 9/1999 | Perdrizet | 424/643 |
| 6,004,744 A | 12/1999 | Goelet et al. | 435/5 |
| 6,013,431 A | 1/2000 | Soderlund et al. | 435/5 |
| 6,133,039 A | 10/2000 | Heinecke | 436/89 |
| 6,291,171 B1 | 9/2001 | Ricciardi et al. | 435/6 |
| 7,211,383 B2 | 5/2007 | DePhillipo et al. | 435/6 |
| 2002/0146698 A1 | 10/2002 | DePhillipo et al. | 435/6 |

FOREIGN PATENT DOCUMENTS

WO WO 02/080755 10/2002
WO WO 2004/026107 4/2004

OTHER PUBLICATIONS

Lucentini, Jack. The Scientist vol. 18:1-5.*
Forsberg et al. Archives of Biochemistry and Biophysics vol. 389:84-93. 2001.*
Hu et al. Cancer Research vol. 63:3347-3351. 2003.*
Fitness et al. Genes and Immunity vol. 3:441-453. 2002.*
Barber et al. J. Med. Genet. vol. 41:808-813. 2004.*
Chistyakov et al. BMC Medical Genetics vol. 2:4-11. 2001.*
Ratnasinghe et al. Cancer Research vol. 60:6381-6383. 2000.*
Millikan et al. Breast Cancer Research vol. 6:264-274. 2004.*
Allen et al. (2000), Immunogenetics, 51:201-205.
Kimura et al. 2000), American Journal of Ophthalmology, 130:769-773.
Kostrikis et al. (1998), Science, 279:1228-1229.
Wood et al. (2001), Science, 291:1284-1289.
Ye et al. (2001), Cancer Research, 61:1296-1298.
Ahmed et al. (200), Journal of the Neurological Sciences, 176:88-94.
Christensen (2001), Science News, 159:156-157.
Koyama et al. (1998), Thorax, 53:10-14.
Ranganthan et al. (2001), The Journal of Biological Chemistry, 276:14264-14270.
Zhang et al. (1999), Cancer Research, 59:6276-6283.

* cited by examiner

*Primary Examiner* — Gary Benzion
*Assistant Examiner* — Cynthia Wilder
(74) *Attorney, Agent, or Firm* — Mintz Levin Cohn Ferris Glovsky and Popeo, P.C.; Ivor R. Elrifi

(57) ABSTRACT

The invention relates to kits and methods for assessing skin health for a human and the human's susceptibility to skin disorders. The methods involve assessing occurrence in the human's genome of one or more polymorphisms (e.g., single nucleotide polymorphisms) that occur in one or more genes associated disclosed herein and that are associated with a disorder in humans. Preferred assessment and scoring methods are disclosed, as are kits for performing the methods.

18 Claims, 1 Drawing Sheet

Fig. 1A

Polymorphism

1  ● ○ ○ ○
    5 2 1 1

2  ○ ●
    2 1

3  ○
    1

4  ○ ○ ○ ● ○ ○ ●
    4 3 3 2 1 1 1

5  ○ ○ ○
    3 1 1

Score = 9

Fig. 1B

Polymorphism

1  ○ ○ ○ ○
    5 2 1 1

2  ○ ●
    2 1

3  ○
    1

4  ○ ○ ○ ● ○ ○ ●
    4 3 3 2 1 1 1

5  ○ ○ ○
    3 1 1

Score = 4

KITS AND METHODS FOR ASSESSING SKIN HEALTH

CROSS-REFERENCE TO RELATED APPLICATIONS

This application is a divisional of U.S. patent application 10/247,935 (filed 20 Sep. 2002), now U.S. Pat. No. 7,211,283 which is a continuation-in-part of International Application No. PCT/US02/10682 (filed 5 Apr. 2002) and of U.S. patent application 09/826,522 (filed 5 Apr. 2001), now abandoned, and is entitled to priority pursuant to 35 U.S.C. §119(e) to U.S. provisional patent applications Nos. 60/289,169 (filed 7 May 2001), 60/350,517 (filed 22 Oct. 2001), 60/335,426 (filed 24 Oct. 2001), and 60/336,815 (filed 5 Dec. 2001).

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Skin is the largest and most visible organ of the human body, and is also among the tissues most exposed to environmental stresses, hazards, and pathogens. Skin is a multi-layered tissue, primarily composed of the epidermis and dermis, and includes several accessory structures, such as sweat glands, sebaceous glands, and hair follicles. Skin serves many functions. For example, it is a protective barrier to external insults (e.g., heat, chemicals, bacteria), is involved in thermoregulation, inhibits dehydration, and performs sensory functions. Skin is also a bioreactor that produces various hormones and lipids that enter the body's circulation. A variety of immune cells function in skin as a first line of defense against bacterial or viral invasion and to maintain immune surveillance in skin and nearby body tissues. For these reasons, establishment and maintenance of good skin health is important to human health.

Skin health is also important for aesthetic reasons. Many people are deeply concerned about the appearance of their skin. A healthy skin appearance is maintained by a combination of cleaning, nutrition, and application of therapeutic and cosmetic products. However, overuse of skin care products can degrade skin health and appearance. Often, individuals employ trial-and-error techniques to identify skin care products (and doses thereof) that produce a desirable skin appearance. More precise methods are needed for identifying compositions (and suitable amounts of such compositions) that will enhance the health and appearance of an individual's skin. These methods would preferably be tailored to identify useful compositions and dosages for individuals. The present invention satisfies this need.

Many skin disorders can be alleviated, inhibited, or even prevented by maintaining a high degree of skin health or by timely intervention with appropriate skin-affecting agents. For example, such intervention can include consuming or topically applying skin care products, modulating sun exposure, adjusting diet, consuming nutritional or pharmaceutical products known to be effective against skin disorders, and undergoing heightened medical monitoring. These changes are often not made, owing to the expense or inconvenience of the changes and an individual's subjective belief that he or she is not at high risk for skin disorders. Improved assessment of skin health can help to identify individuals at risk for developing skin disorders and permit more informed decisions to be made regarding whether lifestyle changes or other interventions are justified.

Many human genes occur in a variety of forms which differ in at least minor ways. Heterogeneity in human genes is believed to have arisen, in part, from minor, non-fatal mutations that have occurred in the genome over time. In some instances, differences between alternative forms of a gene are manifested as differences in the amino acid sequence of a protein encoded by the gene. Some amino acid sequence differences can alter the reactivity or substrate specificity of the protein. Differences between alternative forms of a gene can also affect the degree to which (if at all) the gene is expressed. However, many heterogeneities that occur in human genes appear not to be correlated with any particular phenotype. Known heterogeneities include, for example, single nucleotide polymorphisms (i.e., alternative forms of a gene having a difference at a single nucleotide residue). Other known polymorphic forms include those in which the sequence of larger (e.g., 2-1000 residues) portions of a gene exhibits numerous sequence differences and those which differ by the presence or absence of portion of a gene.

Numerous disorders and physiological states have been correlated with occurrence of one or more alternative forms of an individual gene in the genome of a human who exhibits the disorder or physiological state. For example, Kimura et al. (2000, Am. J. Ophthalmol. 130:769-773) discloses an association between occurrence of a SNP of the manganese superoxide dismutase gene and a form of macular degeneration.

Associations between individual disorders and individual genetic polymorphisms are known. However, disorders can usually result from polymorphisms in any of a relatively large number of genes, and as a result, assessing the polymorphic form(s) of any single gene that occur in a human's genome is usually not predictive of the likelihood that the human will develop the disorder.

A need remains for a method of assessing an individual's skin health or predisposition to develop skin disorders. Such assessment could be used to identify types and amounts of therapeutic, inhibitory, or preventive compositions or interventions that can be used to alleviate, inhibit, or prevent skin disorders. The invention satisfies these needs.

BRIEF SUMMARY OF THE INVENTION

The invention relates to a method of assessing skin health in a human. The method comprises assessing occurrence in the human's genome of disorder-associated polymorphisms in at least two (three, four, five, six, eight, ten, fifteen, or even all) genes selected from the group consisting of
   genes which encode an enzyme that catalyzes conversion of a toxic oxygen species to a less toxic oxygen species;
   genes which encode a protein that provides protection against oxidative stress;
   genes which encode a protein that induces production of a toxic oxygen species;
   genes which encode a protein that indirectly affects oxidative stress;
   genes which encode a protein for which the level of expression of the protein is associated with oxidative stress;
   genes which encode a component of the human DNA repair system; and
   genes which encode a protein associated with production of a toxic oxygen species by a macrophage or polymorphonuclear neutrophilic granulocyte.

It has been discovered that this method is particularly useful for assessing skin health when the genes are selected from the group consisting of
- a) the gene which encodes mitochondrial manganese superoxide dismutase (MnSOD);
- b) the gene which encodes cytoplasmic copper/zinc superoxide dismutase (CZSOD);
- c) the gene which encodes catalase;
- d) the gene which encodes human glutathione peroxidase (hGPX1);
- e) the gene which encodes glutathione S transferase P1 (GSTP1)
- f) the gene which encodes NAD(P)H:quinone oxidoreductase;
- g) the gene which encodes epoxide hydrolase;
- h) the gene which encodes tumor necrosis factor alpha (TNF-alpha);
- i) the gene which encodes NADH/NADPH oxidase p22 subunit (the phox gene);
- j) the gene which encodes nitric oxide synthase;
- k) the gene which encodes cytochrome P450;
- l) the gene which encodes matrix metalloproteinase 1 (MMP-1); and
- m) the gene which encodes profilagrin.

Occurrence of a disorder-associated polymorphism in any of these genes is an indication that the human has poorer skin health than a human whose genome does not comprise the disorder-associated polymorphism, and occurrence of a plurality of disorder-associated polymorphisms is an indication that the human has even poorer skin health than a human whose genome comprises only one of the disorder-associated polymorphisms (and greater still than an individual whose genome does not comprise one of these disorder-associated polymorphisms).

Substantially the same method can be used to assess the advisability that a human should employ a skin care product, such as one comprising a skin protective ingredient or a vitamin (e.g., one of vitamins C and E). When the method is used to assess the advisability that a human should employ a skin care product, occurrence of one or more disorder-associated polymorphisms in any of genes a)-l) is an indication that it is more advisable for the human to use the product than when the individual's genome does not comprise disorder-associated polymorphisms in any of these genes.

For example, occurrence of at least two (three, four, five, six, eight, ten, or fifteen or more) disorder-associated polymorphisms can be assessed, where the polymorphisms are selected from the group consisting of
- A) a polymorphism in the open reading frame encoding mitochondrial MnSOD;
- B) a polymorphism in the open reading frame encoding cytoplasmic CZSOD;
- C) a polymorphism in the promoter region of the gene encoding catalase;
- D) a polymorphism in the open reading frame of the hGPX1 gene;
- E) a polymorphism in the open reading frame encoding glutathione S transferase P1 (GSTP1);
- F) a polymorphism in the open reading frame encoding NAD(P)H:quinone oxidoreductase;
- G) a polymorphism in the open reading frame encoding epoxide hydrolase;
- H) a polymorphism in the promoter region of the gene encoding TNF-alpha;
- I) a polymorphism in the open reading frame of the phox gene;
- J) a polymorphism in the open reading frame encoding nitric oxide synthase;
- K) a polymorphism in the 5' flanking region of the gene encoding cytochrome P450; and
- L) a polymorphism in the promoter region of the gene encoding MMP-1.

Preferably, occurrence of all known polymorphisms at individual sites (e.g., both of two known alternative forms or all three forms of a polymorphism known to exist in three alternative forms) is assessed within an individual's genome, so that the individual's genotype for the polymorphism as that site can be completely known. For example, appropriate polymorphisms that can be assessed in the genes listed above include the following
- i) a polymorphism manifested as occurrence of a codon encoding alanine at amino acid residue 9 (i.e., in the signal sequence) of MnSOD;
- ii) a polymorphism manifested as occurrence of a codon encoding valine at amino acid residue 9 (i.e., in the signal sequence) of MnSOD;
- iii) a polymorphism manifested as occurrence of a codon encoding isoleucine at amino acid residue 58 of MnSOD;
- iv) a polymorphism manifested as occurrence of a codon encoding thymine at amino acid residue 58 of MnSOD;
- v) a polymorphism manifested as occurrence of a codon encoding valine at amino acid residue 7 of CZSOD;
- vi) a polymorphism manifested as occurrence of a codon encoding glutamic acid at amino acid residue 7 of CZSOD;
- vii) a polymorphism manifested as occurrence of a codon encoding cysteine at amino acid residue 6 of CZSOD;
- viii) a polymorphism manifested as occurrence of a codon encoding phenylalanine at amino acid residue 6 of CZSOD;
- ix) a polymorphism manifested as occurrence of a cytosine residue at nucleotide residue −262 (i.e., in the promoter region) of the catalase gene;
- x) a polymorphism manifested as occurrence of a thymine residue at nucleotide residue −262 (i.e., in the promoter region) of the catalase gene;
- xi) a polymorphism manifested as occurrence of a codon encoding proline at amino acid residue 198 of glutathione peroxidase (hGPX1);
- xii) a polymorphism manifested as occurrence of a codon encoding leucine at amino acid residue 198 of glutathione peroxidase (hGPX1);
- xiii) a polymorphism manifested as occurrence of a codon encoding valine at amino acid residue 105 of glutathione S-transferase P1 (GSTP1);
- xiv) a polymorphism manifested as occurrence of a codon encoding isoleucine at amino acid residue 105 of glutathione S-transferase P1 (GSTP1);
- xv) a polymorphism manifested as occurrence of a cytosine residue at nucleotide residue 242 (i.e., in the coding region) of the gene encoding NAD(P)H:quinone oxidoreductase;
- xvi) a polymorphism manifested as occurrence of a thymine residue at nucleotide residue 242 (i.e., in the coding region) of the gene encoding NAD(P)H:quinone oxidoreductase;
- xvii) a polymorphism manifested as occurrence of a thymine residue at nucleotide residue 113 in exon 3 of the gene which encodes epoxide hydrolase (i.e., resulting in a tyrosine residue in epoxide hydrolase);
- xviii) a polymorphism manifested as occurrence of a cytosine residue at nucleotide residue 113 in exon 3 of the gene which encodes epoxide hydrolase (i.e., resulting in a histidine residue in epoxide hydrolase);
xix) a polymorphism manifested as occurrence of an adenine residue at nucleotide residue −238 (i.e., in the promoter region) of the gene which encodes TNF-alpha (i.e., the TNF-alpha promoter variant designated TNF2);
xx) a polymorphism manifested as occurrence of an adenine residue at nucleotide residue −308 (i.e., in the promoter region) of the gene which encodes TNF-alpha (i.e., the TNF-alpha promoter variant designated TNF3);
xxi) a polymorphism manifested as occurrence of a cytosine residue at nucleotide residue 242 (i.e., in the coding region) of the phox gene encoding the NADH/NADPH oxidase p22 subunit;
xxii) a polymorphism manifested as occurrence of a thymine residue at nucleotide residue 242 (i.e., in the coding region) of the phox gene encoding the NADH/NADPH oxidase p22 subunit;
xxiii) a polymorphism manifested as a 27 nucleotide residue repeat in intron 4 (i.e., between nucleotide residues 5130 and 5511) of the gene encoding nitric oxide synthase;
xxiv) a polymorphism manifested as absence of a 27 nucleotide residue repeat in intron 4 (i.e., between nucleotide residues 5130 and 5511) of the gene encoding nitric oxide synthase;
xxv) a polymorphism manifested as occurrence of an adenine residue at nucleotide residue −290 (i.e., in the 5'-flanking region) of the gene encoding cytochrome P450 (i.e., the polymorphism designated the CYP3A4 cytochrome P450 variant);
xxvi) a polymorphism manifested as occurrence of a guanine residue at nucleotide residue −290 (i.e., in the 5'-flanking region) of the gene encoding cytochrome P450 (i.e., the polymorphism designated the CYP3A4 cytochrome P450' variant);
xxvii) a polymorphism manifested as occurrence of a single guanine residue at nucleotide residue −1607 of the human gene encoding MMP-1; and
xxviii) a polymorphism manifested as occurrence of a two consecutive guanine residues at a site including nucleotide residue −1607 of the human gene encoding MMP-1.

Occurrence of an individual disorder-associated polymorphism can be assessed by first contacting a nucleic acid derived from the human's genome with a first oligonucleotide that anneals with higher stringency with the disorder-associated polymorphism than with a corresponding non-disorder-associated polymorphism and then assessing annealing of the first oligonucleotide and the nucleic acid. Annealing of the first oligonucleotide and the nucleic acid is an indication that the human's genome comprises the disorder-associated polymorphism.

Occurrence of an individual disorder-associated polymorphism can be further assessed by contacting the nucleic acid with a second oligonucleotide that anneals with higher stringency with a non-disorder-associated polymorphism than with the corresponding disorder-associated polymorphism and assessing annealing of the second oligonucleotide and the nucleic acid. Annealing of the second oligonucleotide and the nucleic acid is an indication that the human's genome comprises the non-disorder-associated polymorphism. By assessing occurrence of both disorder-associated and non-disorder associated polymorphisms in an individual's genome, one can assess whether the individual is likely homologous for the non-disorder-associated polymorphism, homologous for the disorder-associated polymorphism, or heterozygous for the disorder-associated polymorphism and non-disorder-associated polymorphisms. This information can inform selection of an appropriate agent or intervention and an appropriate dose, duration, or intensity of the agent or intervention for improving skin health or alleviating, inhibiting, or preventing a skin disorder.

A skin health score can be calculated by summing, for each of the selected genes in which a disorder-associated polymorphism occurs in the human's genome, the product of a constant and a correlation factor. The correlation factor can be one or it can, for example, represent the fraction of humans heterozygous or homozygous for the disorder-associated polymorphism who exhibit the corresponding disorder. The skin health score represents the relative susceptibility of the human to a skin disorder.

The same methods can be used to assess the likelihood that a human will develop a skin disorder. Occurrence of any of the disorder-associated polymorphisms is an indication that the human is more susceptible to the skin disorder than a human whose genome does not comprise the polymorphism, and occurrence of a plurality of the disorder-associated polymorphisms is an indication that the human is even more susceptible to the skin disorder than a human whose genome does not comprise the polymorphisms.

These methods can also be used to select a dose of a skin protective composition or other prophylactic or therapeutic composition for administration to a human. Occurrence of any of the disorder-associated polymorphisms is an indication that a greater dose of the composition should be administered to the human. The dose of the composition can be selected based on occurrence of the polymorphisms.

The invention further relates to a kit for assessing relative susceptibility of a human to a skin disorder. The kit comprises reagents for assessing occurrence in the human's genome of disorder-associated polymorphisms in at least two (three, four, five, six, eight, ten, or fifteen or more) of the genes disclosed herein.

In another aspect, the invention relates to a method of assessing the advisability that a human should employ a nutritional product comprising a skin protective agent or other prophylactic or therapeutic composition. The method comprises assessing occurrence in the human's genome of disorder-associated polymorphisms in at least two (three, four, five, six, eight, ten, fifteen, or more) of the genes disclosed herein. Occurrence of any of the disorder-associated polymorphisms is an indication that it is more advisable for the human to employ the nutritional product than a human whose genome does not comprise the polymorphism, and occurrence of a plurality of the disorder-associated polymorphisms is an indication that it is even more advisable that the human should employ the nutritional product than a human whose genome does not comprise the polymorphisms.

In still another aspect, the invention relates to a method of selecting a dose of a skin protective agent for administration to a human in a nutritional product. The method comprises assessing occurrence in the human's genome of disorder-associated polymorphisms in at least two of the genes disclosed herein. Occurrence of any of the polymorphisms is an indication that a greater dose of the agent should be administered to the human in the nutritional product. The dose of the agent for the nutritional product can be selected based on occurrence of the polymorphisms.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. The invention is not limited to the precise arrangements and instrumentalities shown.

FIGS. 1A and 1B are images which depict examples of results that can be obtained by analyzing occurrence of polymorphisms in several genes. The results shown in FIG. 1A are derived from a hypothetical first human, and those shown in FIG. 1B are derived from a hypothetical second human. Circles represent different polymorphisms of the gene indicated to the left of the row of circles. Filled circles indicate the presence of the polymorphism. Non-filled circles indicate the absence of the polymorphism. Numbers below each circle represent a correlation factor for the polymorphism and a disease or disorder (i.e., not necessarily a skin disease or disorder).

DETAILED DESCRIPTION OF THE INVENTION

The invention relates to kits and methods for assessing skin health in a human by assessing occurrence in the human's genome of genetic polymorphisms that are associated with disorders (i.e., any type of disorder, whether a disorder of the skin or not). To better characterize the human's genetic content, occurrence of polymorphic forms (of the same genes) that are not associated with a disorder can also be assessed, so that one can determine whether the human is 1) homozygous for the disorder-associated polymorphism at a genomic site, 2) heterozygous for disorder-associated and non-disorder-associated polymorphisms at that site, or 3) homozygous for non-disorder-associated polymorphisms at that site. Assessments of genomic polymorphism content in two or more (and preferably in three, four, five, six, eight, ten, fifteen, or more) of the genes identified herein as being significant to skin health can be combined to indicate the skin health of the human. This assessment of skin health can be used to predict the likelihood that the human will develop, is developing, is predisposed to develop, or has already developed a skin disorder.

Crudely simplified, the methods involve determining whether multiple polymorphisms that have been associated (by the inventors or by others) with a human disorder (i.e., a disease or pathological state, whether of the skin or not) occur in the genome of the human being tested. In some embodiments, the number of polymorphisms that occur in the human's genome are summed to yield a value; the higher the value is, the greater the susceptibility of the human to skin disorders is assessed to be (i.e., the poorer the human's skin health is assessed to be). In other embodiments, a weighting factor is assigned to each polymorphism tested, and the weighting factors of polymorphisms that occur in the human's genome are summed to yield a value that represents relative skin health (e.g., as assessed by susceptibility to skin disorders). The weighting factor can represent the product of a constant assigned to the gene in which the corresponding polymorphism occurs and a correlation factor that describes how informative occurrence of the polymorphism is for occurrence of the disorder with which it is associated. The weighting factor can also be influenced by whether the human is homozygous or heterozygous for the disorder-associated polymorphism. The invention includes a variety of alternative methods and kits for performing the methods, as described in greater detail herein.

Definitions

As used in this disclosure, the following terms have the meanings associated with them in this section.

A "polymorphism" in a gene is one of the alternative forms of a portion of the gene that are known to occur in the human population. For example, many genes are known to exhibit single nucleotide polymorphic forms, whereby the identity of a single nucleotide residue of the gene differs among the forms. Each of the polymorphic forms represents a single polymorphism, as the term is used herein. Other known polymorphic forms include alternative forms in which multiple consecutive or closely-spaced, non-consecutive nucleotide residues vary in sequence, forms which differ by the presence or absence of a single nucleotide residue or a small number of nucleotide residues, and forms which exhibit different mRNA splicing patterns.

A "single nucleotide polymorphism" ("SNP") is one of the alternative forms of a portion of a gene that vary only in the identity of a single nucleotide residue in that portion.

A "disorder-associated" polymorphism is an alternative form of a portion of a gene, wherein occurrence of the alternative form in the genome of a human has been correlated with exhibition by the human of a disease or a pathological state, whether the disease or pathological state affects the skin, another tissue, or multiple tissues.

A "non-disorder-associated" polymorphism is an alternative form of a portion of a gene for which no significant positive correlation has been made between occurrence of the alternative form in the genome and occurrence of a disease or a pathological state. Non-disorder-associated polymorphisms are sometimes designated "neutral" polymorphisms in the art.

A disorder-associated polymorphism and a non-disorder-associated polymorphism "correspond" with one another if the two polymorphisms are two alternative forms of the same portion of the gene. By way of example, if the identity of residue 100 of a gene is adenine in a disorder-associated polymorphism of the gene and cytosine in a non-disorder-associated polymorphism of the gene, then the two polymorphisms correspond with one another. It is understood that there may be three or more corresponding polymorphisms when there are more than two alternative forms of the same portion of the gene.

A "characteristic residue" of a polymorphism is a nucleotide residue, the identity of which is known to vary among the alternative forms corresponding to the polymorphism.

A "skin disorder" is a pathological condition characterized by dysfunction, (e.g., inflammation, necrosis, abnormal proliferation, reduced elasticity, defective renewal, irritation, or infection) of some portion of the skin.

"Skin health" is a measure of the absence of a skin disorder in an individual human (i.e., characterized by normal skin function and appearance) and the likelihood that the individual will continue to exhibit absence of a skin disorder.

"Toxic oxygen species" include, in approximate order of decreasing reactivity, hydroxyl radicals, superoxide radicals, nitric oxide, peroxy nitrite ($ONOO^-$; the product of a reaction between nitric oxide and superoxide radical), and hydrogen peroxide. Ordinary diatomic oxygen is not a toxic oxygen species, as the term is used herein.

"Oxidative damage" refers to chemical reaction of a normal cellular component (e.g., DNA, a protein, or a lipid) with a toxic oxygen species, whereby at least one normal function of the component is inhibited or eliminated. The terms "oxidative damage" and "oxidative stress" are used interchangeably herein.

A "molecular beacon oligonucleotide" is a single-stranded oligonucleotides having a fluorescent label (e.g., rhodamine, FAM, TET, VIC, JOE, or HEX) attached to the 5'-end thereof and a fluorescence quencher (e.g., TAMRA or DABCYL) attached to the 3'-end thereof (or vice versa), as described (Kostrikis et al., 1998, Science 279:1228-1229).

Two molecular beacon oligonucleotides are "spectrally distinct" if they can be differentially detected using spectrophotometric or spectrofluorimetric methods. Examples of characteristics that can be used to differentiate spectrally distinct oligonucleotides include absorption or excitation wavelength, emission wavelength, and fluorescent lifetime.

An "instructional material" is a publication, a recording, a diagram, or any other medium of expression which can be used to communicate how to use a kit described herein, numerical values for weighting the significance of various polymorphisms that are detectable using the kit, or both. The instructional material of the kit of the invention can, for example, be affixed to a container which contains a kit of the invention or be shipped together with a container which contains the kit. Alternatively, the instructional material can be shipped separately from the container with the intention that the instructional material and the kit be used cooperatively by the recipient.

The "stringency" with which two polynucleotides anneal means the relative likelihood that the polynucleotides will anneal in a solution as the conditions of the solution become less favorable for annealing. Examples of stringent conditions are known in the art and can be found in available references (e.g., Current Protocols in Molecular Biology, John Wiley & Sons, N.Y., 1989, 6.3.1-6.3.6). Aqueous and non-aqueous annealing methods are described in that reference and either can be used. In general, a first pair of polynucleotides anneal with higher stringency than a second pair if the first pair is more likely to anneal (or remain annealed) as one or more of the salt concentration, temperature, and detergent concentration are increased.

With respect to a disorder, a "correlation factor" for a disorder-associated polymorphism is the fractions of humans who are heterozygous or homozygous for the polymorphism who exhibit the disorder. The correlation factor can, alternatively, be based solely on those who are heterozygous, solely on those who are homozygous, or on those who are either heterozygous or homozygous.

A "non-extendable" nucleotide residue is a nucleotide residue that is capable of being added to a polynucleotide by a polymerase (i.e., by extension of the polynucleotide in association with a complement thereof, catalyzed by the polymerase) and that, upon addition to the polynucleotide, renders the polynucleotide incapable of being further extended by the polymerase.

Description

The invention relates to kits and methods for assessing the skin health of a human by assessing occurrence in the human's genome of genetic polymorphisms that are associated with disorders (i.e., skin disorders or other disorders). Unlike other methods that predict susceptibility to a disorder based on occurrence of a particular polymorphism in a particular gene, a panel of informative genes and polymorphisms is disclosed herein. Using two or more of the genes in this panel, one can assess the susceptibility of a human to a skin disorder, even if the skin disorder has not been specifically associated with occurrence of a polymorphism in the panel.

It has been discovered an individual's skin health can be assessed by determining the polymorphic forms of certain genes that are present in the individual's genome. The genes which are assessed are disclosed herein. Assessment of disorder-associated polymorphisms in two or more of these genes (preferably three, four, five, six, eight, ten, fifteen, or more of these genes) in a human's genome is predictive of the human's skin health. The greater the number of these genes in which occurrence of disorder-associated polymorphisms is assessed, the greater the precision of the methods for predicting the human's skin health is likely to be. Occurrence in the individual's genome of other polymorphisms (e.g., ones known to be associated with occurrence of the skin disorder of interest) can also be assessed concurrently or sequentially.

Skin disorders for which the kits and methods described herein are useful include inflammatory disorders (e.g., contact dermatitis, uticaria, atopic dermatitis, psoriasis, lichen planus, cutaneous lupus erythematosus, pemphigus, and scleroderma, sun damage (e.g., reddening and sun burn), infectious diseases (e.g., bacterial and viral infections), and skin tumors (e.g., keratoses, squamous cell carcinomas, basal cell carcinomas, melanomas, and Kaposi's sarcoma).

Susceptibility of an individual to a skin disorder can be affected by oxidative stress that skin cells experience. Several of the genes having polymorphic forms that are informative for skin health encode proteins that modulate the body's response to or protection from oxidative stress. For example, genes which protect against oxidative stress include genes which encode an enzyme that catalyzes conversion of a toxic oxygen species to a less toxic oxygen species, genes that encode a protein that directly provides protection against oxidative damage, genes which encode a protein that indirectly provides protection against oxidative damage, genes which encode a component of the human DNA repair system, and genes (not necessarily included within the preceding groups) which are associated with inducible production of reactive oxygen species in immune cells following microbial infection.

Polymorphisms have been identified in some, if not all, of the numerous genes that encode components of the human DNA repair system. Disorder-associated polymorphisms in these genes can be informative for the skin health of an individual (e.g., for susceptibility of the individual to a skin disorder). Examples of these genes include those which encode apurinic and apyrimidinic endonucleases, enzymes that catalyze excision of nucleotide residues damaged by ultraviolet radiation, and enzymes that catalyze site specific-recombination. Many such genes are known, and include those listed in Wood et al., 2001, Science 291(5507):1284-1289.

Skin comprises immune cells and acts as a first line of defense against microbial invasion. Genes that induce production of reactive oxygen species in immune cells following microbial infection include genes (e.g., genes which encode components of the human phagocyte-specific NADPH-oxidase complex) associated with respiratory burst (sometimes designated oxidative burst) phenomena of macrophages and polymorphonuclear nucleophilic granulocytes, whereby toxic oxygen species are produced in response to invasion of a tissue by a microbe (e.g., a protozoan, or a bacterium such as a *Pseudomonas, Salmonella*, or *Serratia* bacterium or a known pathogen such as *Bacillus anthracis, Escherichia coli*, or *Staphylococcus aureus*). Also included within this group are genes which are known to be aberrant in patients afflicted with disorders that inhibit or abolish antimicrobial activities of macrophages (e.g., chronic granulomatous disease). Disorder-associated polymorphisms in substantially any of these genes can be informative of the susceptibility of the individual to a skin disorder, particularly a skin infection or inflammatory skin disorder. Identification of individuals in whom such polymorphisms occur (e.g., using the methods described herein) can be used, for example, to assess whether an individual has an elevated risk for developing a skin disorder and whether some disorder inhibits intervention should be undertaken.

It is not critical that the gene in which the occurrence of a polymorphism occurs is recognized as being directly or indirectly involved in a skin disorder. It is sufficient that an association can be made between either the level of expression of the gene or the sequence of the gene product and skin health of humans.

Skin disorders include allergic reactions, such as hives and contact dermatitis. Genes that encode enzymes that catalyze reactions responsible for decreasing electrophilic potential of allergens (or their metabolites), a process designated biotransformation of allergens, can affect the skin health of a human. Members of the glutathione S-transferase (GST) family of enzymes, such as GSTP1, participate in the biotransformation of allergens. These enzymes also catalyze interconversions among reactive forms of oxygen. Occurrence of one or more polymorphism in one of these GST genes can be used to assess skin health of an individual.

Another protein involved in production of toxic oxygen species by components of the immune system in response to allergen exposure is TNF-alpha. Allen et al. (2000, Immunogenetics 51:201-205) described a polymorphism that occurs at nucleotide residue −308 (i.e., in the promoter region) of the gene that encodes TNF-alpha. This polymorphism can be one of those assessed as described herein.

Among enzymes that catalyze conversion of a toxic oxygen species to a less toxic oxygen species, four are of particular relevance, namely mitochondrial MnSOD, cytoplasmic CZSOD, catalase (CAT), and glutathione peroxidase (GP). Polymorphisms that occur in these genes are known to be associated with various disorders (see, e.g., Kimura et al., 2000, Am. J. Ophthalmol. 130:769-773). Occurrence of disorder-associated polymorphisms in at least one (and preferably two, three, or all) of these four genes should be assessed in the methods described herein, given the importance of these genes. Similarly, the kits described herein preferably include reagents for detecting disorder-associated polymorphisms in at least one (and preferably two, three, or all) of these four genes. In addition, the significance of occurrence of disorder-associated polymorphisms in these genes can be applied by assigning a greater weighting factor to disorder-associated polymorphisms of these genes than to disorder-associated polymorphisms in other genes disclosed herein.

Genes in which disorder-associated polymorphisms occur that are useful for assessing the skin health of an individual include genes which encode an enzyme that catalyzes conversion of a toxic oxygen species to a less toxic oxygen species;
genes which encode a protein that provides protection against oxidative stress;
genes which encode a protein that induces production of a toxic oxygen species;
genes which encode a protein that indirectly affects oxidative stress;
genes which encode a protein for which the level of expression of the protein is associated with oxidative stress;
genes which encode a component of the human DNA repair system; and
genes which encode a protein associated with production of a toxic oxygen species by a macrophage or polymorphonuclear neutrophilic granulocyte.

It has been discovered that the following genes are of particular relevance to skin health:
a) the gene which encodes mitochondrial MnSOD;
b) the gene which encodes cytoplasmic CZSOD;
c) the gene which encodes catalase;
d) the gene which encodes hGPX1;
e) the gene which encodes GSTP1
f) the gene which encodes NAD(P)H:quinone oxidoreductase;
g) the gene which encodes epoxide hydrolase;
h) the gene which encodes TNF-alpha;
i) the phox gene;
j) the gene which encodes nitric oxide synthase;
k) the gene which encodes cytochrome P450;
l) the gene which encodes MMP-1; and
m) the gene which encodes profilagrin.

Occurrence in a patient's genome of a disorder-associated polymorphism in one of genes a)-l) is an indication that the patient is at a greater risk of developing a skin disorder (or is already afflicted with the disorder) than a human whose genome does not include the disorder-associated polymorphism. Occurrence of multiple disorder-associated polymorphisms in these genes in a patient's genome is an indication that that patient is at greater risk for developing a skin disorder (i.e., has poorer skin health) than a human in whose genome fewer (or none) of the disorder-associated polymorphisms occur. Thus, there is a cumulative effect of disorder-associated polymorphisms in the genes identified herein on the skin health of the human in which they occur.

Occurrence of two copies of the same disorder-associated polymorphism in the same human (i.e., homozygosity for the disorder-associated polymorphism) is an indication that the human is at a greater risk for developing a skin disorder (i.e., has poorer skin health) than a human in whom only a single copy of the polymorphism occurs (i.e., an individual heterozygous for the disorder-associated polymorphism). Homozygosity for the disorder-associated polymorphism can be accounted for by more heavily weighting occurrence of two copies of the disorder-associated polymorphism than occurrence of only a single copy (e.g., by multiplying the significance associated with occurrence of the disorder-associated polymorphism by a factor such as two, five, ten or another value).

Although the invention is not limited to the particular disorder-associated polymorphisms in the genes identified herein, it is recognized that disorder-associated polymorphisms that occur in particular portions of the genes can be more significant indicators of skin health than disorder-associated polymorphisms that occur in particular portions of the genes. Thus, disorder-associated polymorphisms that occur in the following regions of the indicated genes can be weighted more heavily than disorder-associated polymorphisms that occur in other portions of the genes. These polymorphisms include A) disorder-associated polymorphisms in the open reading frame encoding mitochondrial MnSOD;
B) disorder-associated polymorphisms in the open reading frame encoding cytoplasmic CZSOD;
C) disorder-associated polymorphisms in the promoter region of the gene encoding catalase;
D) disorder-associated polymorphisms in the open reading frame encoding hGPX1;
E) disorder-associated polymorphisms in the open reading frame encoding GSTP1;
F) disorder-associated polymorphisms in the open reading frame encoding NAD(P)H:quinone oxidoreductase;
G) disorder-associated polymorphisms in the open reading frame encoding epoxide hydrolase;
H) disorder-associated polymorphisms in the promoter region of the gene encoding TNF-alpha;
I) disorder-associated polymorphisms in the open reading frame of the phox gene;
J) disorder-associated polymorphisms in the open reading frame encoding nitric oxide synthase;
K) disorder-associated polymorphisms in the 5' flanking region of the gene encoding cytochrome P450; and L) disorder-associated polymorphisms in the promoter region of the gene encoding MMP-1.

Occurrence of any of a number of particular polymorphisms can be assayed in order to assess an individual's skin health. A non-limiting list of such polymorphisms include the following:

I) a polymorphism manifested as a change from an alanine residue to a valine residue at amino acid residue 9 (i.e., in the signal sequence) of mitochondrial MnSOD;

II) a polymorphism manifested as a change from an isoleucine residue to a thymine residue at amino acid residue 58 of mitochondrial MnSOD;

III) a polymorphism manifested as a change from a valine residue to a glutamic acid residue at amino acid residue 7 of cytoplasmic CZSOD;

IV) a polymorphism manifested as a change from a cysteine residue to a phenylalanine residue at amino acid residue 6 of cytoplasmic CZSOD;

V) a polymorphism manifested as a change from a cytosine residue to a thymine residue at nucleotide residue −262 (i.e., in the promoter region) of the catalase gene;

VI) a polymorphism in the hGPX1 gene manifested as a change from a proline residue to a leucine residue at amino acid residue 198 of glutathione peroxidase;

VII) a polymorphism in the GSTP1 gene manifested as a change from a valine residue to an isoleucine residue at amino acid residue 105 of glutathione S-transferase P1;

VIII) a polymorphism manifested as a change from a cytosine residue to a thymine residue at nucleotide residue 242 (i.e., in the coding region) of the gene encoding NAD(P)H:quinone oxidoreductase;

IX) a polymorphism manifested as a change from a thymine residue to a cytosine residue at nucleotide residue 113 in exon 3 of the gene which encodes epoxide hydrolase (i.e., effecting change of from a tyrosine residue to a histidine residue in epoxide hydrolase);

X) a polymorphism manifested as a change to an adenine residue at nucleotide residue −238 (i.e., in the promoter region) of the gene which encodes TNF-alpha (i.e., the TNF-alpha promoter variant designated TNF2);

XI) a polymorphism manifested as a change to an adenine residue at nucleotide residue −308 (i.e., in the promoter region) of the gene which encodes TNF-alpha (i.e., the TNF-alpha promoter variant designated TNF3);

XII) a polymorphism manifested as a change from a cytosine residue to a thymine residue at nucleotide residue 242 (i.e., in the coding region) of the phox gene encoding the NADH/NADPH oxidase p22 subunit;

XIII) a polymorphism manifested as a 27 nucleotide residue repeat in intron 4 (i.e., between nucleotide residues 5130 and 5511) of the gene encoding nitric oxide synthase;

XIV) a polymorphism manifested as a change from an adenine residue to a guanine residue at nucleotide residue −290 (i.e., in the 5'-flanking region) of the gene encoding cytochrome P450 (i.e., the polymorphism designated the CYP3A4 cytochrome P450 variant); and XV) a polymorphism manifested as occurrence of a two consecutive guanine residues at a site including nucleotide residue −1607 of the human gene encoding MMP-1.

Occurrence of a disorder-associated polymorphism in an individual's genome can be assessed in any of a variety of ways. In one embodiment, a simple test (e.g., primer extension, PCR amplification, or molecular beacon oligonucleotide-binding) is used to determine whether or not the disorder-associated polymorphism occurs in the individual's genome (i.e., without regard to copy number). In another embodiment, a test is used to determine whether the individual's genome includes a non-disorder-associated polymorphism corresponding to a known disorder-associated polymorphism in a gene disclosed herein (i.e., as an indication that the individual is at least heterozygous for the non-disorder-associated polymorphism). In yet another embodiment, a test (i.e., using multiple probes or primers) is used that is able to detect both disorder-associated polymorphisms and non-disorder-associated polymorphisms in two, three, four, or more genes disclosed herein. Using such a test, one can determine both occurrence of a disorder-associated polymorphism in an individual's genome and whether the individual is homozygous or heterozygous for the disorder-associated polymorphism. This test also permits 'checking' of results, since it can both account for all known polymorphic forms and indicate when a previously uncharacterized polymorphism occurs at or near the site of a known polymorphism.

In a kit or method for detecting both disorder-associated polymorphisms and non-disorder-associated polymorphisms known for the genes disclosed herein, one or more (preferably at least two, three, four, five, six, eight, ten, or fifteen or more) of the following polymorphisms can be assessed:

i) a polymorphism manifested as occurrence of a codon encoding alanine at amino acid residue 9 (i.e., in the signal sequence) of mitochondrial MnSOD;

ii) a polymorphism manifested as occurrence of a codon encoding valine at amino acid residue 9 (i.e., in the signal sequence) of mitochondrial MnSOD;

iii) a polymorphism manifested as occurrence of a codon encoding isoleucine at amino acid residue 58 of mitochondrial MnSOD;

iv) a polymorphism manifested as occurrence of a codon encoding thymine at amino acid residue 58 of mitochondrial MnSOD;

v) a polymorphism manifested as occurrence of a codon encoding valine at amino acid residue 7 of cytoplasmic CZSOD;

vi) a polymorphism manifested as occurrence of a codon encoding glutamic acid at amino acid residue 7 of cytoplasmic CZSOD;

vii) a polymorphism manifested as occurrence of a codon encoding cysteine at amino acid residue 6 of cytoplasmic CZSOD;

viii) a polymorphism manifested as occurrence of a codon encoding phenylalanine at amino acid residue 6 of cytoplasmic CZSOD;

ix) a polymorphism manifested as occurrence of a cytosine residue at nucleotide residue −262 (i.e., in the promoter region) of the catalase gene;

x) a polymorphism manifested as occurrence of a thymine residue at nucleotide residue −262 (i.e., in the promoter region) of the catalase gene;

xi) a polymorphism in the hGPX1 gene manifested as occurrence of a codon encoding proline at amino acid residue 198 of glutathione peroxidase;

xii) a polymorphism in the hGPX1 gene manifested as occurrence of a codon encoding leucine at amino acid residue 198 of glutathione peroxidase;

xiii) a polymorphism in the GSTP1 gene manifested as occurrence of a codon encoding valine at amino acid residue 105 of glutathione S-transferase P1;

xiv) a polymorphism in the GSTP1 gene manifested as occurrence of a codon encoding isoleucine at amino acid residue 105 of glutathione S-transferase P1;

xv) a polymorphism manifested as occurrence of a cytosine residue at nucleotide residue 242 (i.e., in the coding region) of the gene encoding NAD(P)H:quinone oxidoreductase;

xvi) a polymorphism manifested as occurrence of a thymine residue at nucleotide residue 242 (i.e., in the coding region) of the gene encoding NAD(P)H:quinone oxidoreductase;

xvii) a polymorphism manifested as occurrence of a thymine residue at nucleotide residue 113 in exon 3 of the gene which encodes epoxide hydrolase (i.e., resulting in a tyrosine residue in epoxide hydrolase);

xviii) a polymorphism manifested as occurrence of a cytosine residue at nucleotide residue 113 in exon 3 of the gene which encodes epoxide hydrolase (i.e., resulting in a histidine residue in epoxide hydrolase);

xix) a polymorphism manifested as occurrence of an adenine residue at nucleotide residue −238 (i.e., in the promoter region) of the gene which encodes TNF-alpha (i.e., the TNF-alpha promoter variant designated TNF2);

xx) a polymorphism manifested as occurrence of an adenine residue at nucleotide residue −308 (i.e., in the promoter region) of the gene which encodes TNF-alpha (i.e., the TNF-alpha promoter variant designated TNF3);

xxi) a polymorphism manifested as occurrence of a cytosine residue at nucleotide residue 242 (i.e., in the coding region) of the phox gene encoding the NADH/NADPH oxidase p22 subunit;

xxii) a polymorphism manifested as occurrence of a thymine residue at nucleotide residue 242 (i.e., in the coding region) of the phox gene encoding the NADH/NADPH oxidase p22 subunit;

xxiii) a polymorphism manifested as a 27 nucleotide residue repeat in intron 4 (i.e., between nucleotide residues 5130 and 5511) of the gene encoding nitric oxide synthase;

xxiv) a polymorphism manifested as absence of a 27 nucleotide residue repeat in intron 4 (i.e., between nucleotide residues 5130 and 5511) of the gene encoding nitric oxide synthase;

xxv) a polymorphism manifested as occurrence of an adenine residue at nucleotide residue −290 (i.e., in the 5'-flanking region) of the gene encoding cytochrome P450 (i.e., the polymorphism designated the CYP3A4 cytochrome P450 variant);

xxvi) a polymorphism manifested as occurrence of a guanine residue at nucleotide residue −290 (i.e., in the 5'-flanking region) of the gene encoding cytochrome P450 (i.e., the polymorphism designated the CYP3A4 cytochrome P450 variant);

xxvii) a polymorphism manifested as occurrence of a single guanine residue at nucleotide residue −1607 of the human gene encoding MMP-1; and xxviii) a polymorphism manifested as occurrence of a two consecutive guanine residues at a site including nucleotide residue −1607 of the human gene encoding MMP-1.

Another important set of polymorphisms that can be assessed in order to determine an overall skin health score for a human are disorder-associated polymorphisms that occur in the human profilagrin gene. Numerous polymorphic forms of these gene are known, and the associations of each of these forms with one or more disorders is not yet fully characterized. Of course, whenever a profilagrin polymorphic form is or becomes associated with a disorder, occurrence of that disorder-associated polymorphic form of the profilagrin gene can be used to assess skin health in a human. Known profilagrin polymorphisms include SNPs and filagrin-polymer-length polymorphisms. This latter term refers to the number of filagrin polypeptides into which the profilagrin polypeptide is post-translationally cleaved in a human cell. Various individual humans are known to harbor profilagrin genes that encode a profilagrin with at least 9 to 12 filagrin units.

An important aspect of this invention is that human skin health (e.g., susceptibility to a skin disorder such as psoriasis, eczema, a skin cancer, or a bacterial infection) can be associated with occurrence in the human's genome of a disorder-associated polymorphism in one of the genes described herein—even if there is no known biochemical or physiological association between occurrence of the polymorphism and skin health or incidence of a skin disorder. Put another way, the present inventors have discovered that genes and polymorphisms disclosed herein are predictive indicators of the state of an individual human's skin health. By assessing whether or not disorder-associated polymorphisms occur in the genes identified herein in an individual (and how many such polymorphisms occur in those genes), one can assess the individual's skin health (e.g., as manifested as the likelihood that the individual has, or will develop a skin disorder).

If it is determined that an individual has poor skin health (e.g., because multiple disorder-associated polymorphisms occur in the individual's genome in the genes disclosed herein), then the individual can be encouraged to make changes to improve their skin health, skin appearance, or to reduce the likelihood of developing skin disorders. Such changes can include use of skin protective compositions (e.g., nutritional formulas including anti-oxidants, sunscreens, and topical or system corticosteroids), use of cosmetic compositions, improving nutrition, and avoiding sunlight. Determination that an individual has relatively poor skin health can also be used as an indication that the individual should be monitored more closely than others for development of skin disorders.

Early detection of a predisposition to develop a skin disorder can enable an individual (or the individual's physician) to take steps to delay, inhibit, alleviate (i.e., reduce the severity of), or even prevent the disorder. The appropriate steps for treating and preventing skin disorders are well known and include modifying diet, exercise, and intake or topical application of nutrients and pharmaceuticals. Palliative, therapeutic, and prophylactic methods are known for many skin disorders, and these can be undertaken once a patient's susceptibility to the disorder is known. Thus, the kits and methods described herein permit a skin disorder to be treated, inhibited, or prevented. The kits and methods described herein allow these interventions to be made at an early stage of the skin disorder (when treatment is often most effective), or even before the disorder is symptomatically manifested.

It was not previously appreciated that detection in a human's genome of two or more disorder-associated polymorphisms in the genes disclosed herein is indicative that the human exhibits poorer skin health, manifested as greater susceptibility to skin disorders than individuals having a genome containing fewer (or none) of these disorder-associated polymorphisms. Previous studies are believed to have recognized only association between a polymorphism in only individual genes identified herein and a particular disorder. The inventors believe that they are the first to describe methods and kits for assessing a human's susceptibility to skin disorders based on occurrence in the human of certain polymorphisms that are not recognized as being associated with the individual skin disorder.

It has been discovered that disorder-associated polymorphisms that occur in the genes identified herein as a)-l) can be used to assess both an individual's skin health and the likelihood that the individual will develop (or is currently afflicted with) a skin disorder. In one embodiment of the kits and method described herein, occurrence of disorder-associated polymorphisms (and/or non-disorder-associated polymorphisms) is assessed in two or more of the genes identified herein as a)-l), such as occurrence of a disorder-associated polymorphisms identified herein as A)-L). By way of example, the kit or method can involve assessing occurrence of multiple polymorphisms identified herein as i)-xxviii).

Methods of Assessing Skin Health

The invention includes a method of assessing the skin health (e.g., relative susceptibility to one or more skin disorders) of a human. Skin health can be calculated relative to a hypothetical human whose genome does not contain a single disorder-associated polymorphism in a gene disclosed herein. Alternatively, susceptibility can be calculated relative to another human who may have one or more different disorder-associated polymorphism than the human being assessed. In practice, the basis upon which raw susceptibility scores are calculated is immaterial, so long as the same basis is used for all humans whose scores are to be compared (i.e., so that the scores are relatable to one another).

The relative skin health of a human can be used to assess the risks and benefits of a variety of compositions, conditions, and interventions. In one embodiment, the skin health of a human can be used to determine whether the human would benefit by supplementing nutritional intake with a composition that contains one or more vitamins, minerals, or other skin protective agents. Numerous skin protective agents are known and additional agents are certain to be discovered over time. The usefulness of the kits and methods disclosed herein does not depend on the identity of the particular agent. Examples of skin protective agents include vitamins (especially anti-oxidant vitamins), minerals, naturally-occurring amino acids, derivatives of naturally-occurring amino acids, plant extracts, and conventional skin care products (e.g., skin softening and moisturizing lotions, Aloe extracts, and the like). Anti-oxidant vitamins are preferably administered to skin in a protein-complexed form (e.g., using preparations such as the VITAZYME® vitamin preparations sold by Arch Personal Care Products, L.P. of South Plainfield, N.J.). Similarly, skin protective minerals such as manganese and selenium are also preferably administered to skin in a protein-complexed form (e.g., using preparations such as the ACQUA-BIOMIN™ mineral preparations sold by Arch Personal Care Products, L.P.). Useful skin protective plant extracts include gape polyphenols and naturally active botanicals (NABs) such as NAB Pikea robusta (red algae) extract, NAB fennel seed (*Foeniculum vulgare*) extract, and NAB red clover (*Trifollum Pratense*) leaf extract. Useful naturally-occurring amino acids and derivatives thereof include glycine, glutamine, N-acetylcysteine, and trimethylglycine. Furthermore, the skin health, as assessed using a kit or method as described herein, can indicate an appropriate dose of such an agent for an individual patient.

The skin protective agent that is administered to an individual subject can be determined by the overall skin health score, by observing the genes in which disorder-associated polymorphisms occur, or both.

For example, if a disorder-associated polymorphism occurs in the subject's MnSOD gene, then a manganese-containing skin protective agent, a zinc-containing skin protective agent, or a manganese- and zinc-containing skin protective agent (e.g., one of the ACQUA BIOMIN™ products) can be applied to the subject's skin to inhibit or alleviate skin disorders.

If a disorder-associated polymorphism occurs in the subject's glutathione peroxidase gene, then a skin protective agent comprising one or more of selenium, grape polyphenols, N-acetylcysteine, glutamine, glycine, or NAB fennel seed can be applied to the subject's skin to inhibit or alleviate skin disorders.

If a disorder-associated polymorphism occurs in the subject's microsomal epoxide hydrolase gene, then a skin protective agent comprising one or more of N-acetylcysteine, trimethylglycine, an anti-oxidant vitamin (e.g., one of the VITAZYME® products), NAB Pikea robusta, and NAB fennel seed can be applied to the subject's skin to inhibit or alleviate skin disorders.

If a disorder-associated polymorphism occurs in the subject's tumor necrosis factor-alpha gene, then a skin protective agent comprising one or both NAB Pikea robusta and NAB red clover leaf can be applied to the subject's skin to inhibit or alleviate skin disorders.

Skin health of a human is determined by assessing occurrence in the human's genome of disorder-associated polymorphisms in a plurality of genes disclosed herein (e.g., 2, 3, 4, 6, 8, 10, 15, or more genes). Occurrence of a disorder-associated polymorphism in one of these genes is an indication that the human has a greater susceptibility to skin disorders and poorer skin health than a human in whose genome the polymorphism does not occur. Occurrence of two or more such polymorphisms in the human's genome indicates that the human exhibits even greater susceptibility to skin disorders (and poorer skin health).

Occurrence of each disorder-associated polymorphism in a gene disclosed herein is not necessarily equally indicative of susceptibility to skin disorders and poorer skin health. In order to account for differences in the significance of various disorder-associated polymorphisms, a weighting factor can be assigned to each polymorphism detected in the methods and kits described herein. As indicated above, some genes have a more significant role in skin health in humans than others. Generally, disorder-associated polymorphisms that occur in one of these genes are more significant than polymorphisms that occur in genes having less significant roles in skin health. Thus, a greater weighting factor can be assigned to these polymorphisms than to others. By way of example, the weighting factor assigned to these polymorphisms can be 1 to 10 times greater than the weighting factor assigned to disorder-associated polymorphisms in other genes.

Another factor which can influence the significance that is assigned to occurrence of a disorder-associated polymorphism in a human's genome is the degree to which the polymorphism is correlated with the corresponding disorder. Some disorders are highly correlated with occurrence of a genetic polymorphism, and other disorders exhibit lower correlation with a polymorphism. When a polymorphism is reported to be associated with a disorder (i.e., with a disease or pathological condition), a degree of correlation between the polymorphism and the disorder can be determined or obtained from reports in the literature. One useful way of calculating a factor that describes correlation between a polymorphism and a disorder is to calculate an odds ratio that describes the likelihood that an individual in whose genome the disorder-associate polymorphism occurs will exhibit or develop the disorder. Because the kits and methods described herein can be used to detect whether the human is homozygous for the disease-associated polymorphism, odds ratios calculated for homozygous individuals can also be used, if they are available. Odds ratios can be calculated as described in the art.

For a disorder-associated polymorphism, the odds ratio can be calculated as follows. First, the odds of being afflicted with the disorder are calculated for a first population in which the polymorphism occurs by dividing the number of afflicted individuals in the first population by the total number of individuals in the first population. Second, the odds of being afflicted with the disorder are calculated for a first population in whom the polymorphism does not occur by dividing the number of afflicted individuals in the second population by the total number of individuals in the second population. Third, the odds ratio is calculated by dividing the odds for the first population by the odds for the second population. If the odds ratio is greater than one, then this is an indication that occurrence of the polymorphism is associated with occurrence of the disorder. Furthermore, the magnitude of the odds ratio is an indication of the significance of the association.

A skin health score for a human can be determined as follows. A significance score can be assigned to each disorder-associated polymorphism that is detected in the human's genome using a method or kit described herein. The significance score is a constant (e.g., 1.00), and is multiplied by any significance factor (e.g., 1-10) and by any correlation factor that is available. If information is available which describes the correlation between homozygosity for the polymorphism and the corresponding disorder, then that correlation factor should be used in place of the correlation factor for mere occurrence of the polymorphism, at least if the method or kit is used to rule out occurrence in the subject's genome of corresponding disorder-non-associated polymorphisms. If significance and correlation factors are not available, then values of 1.00 should be assigned to each. The skin health score is determined by summing the significance score for each disorder-associated polymorphism that is detected using the method or kit. This skin health score can be compared with the values obtained from other subjects, or it can be compared with the value (i.e., zero) which would be expected to occur in a human whose genome does not include any disorder-associated polymorphism in a gene disclosed herein. A high skin health score corresponds to poor skin health. Thus, for two individuals having different skin health scores, the individual having the lower score has better skin health than the individual having the higher score.

The method used to assess occurrence of any particular disorder-associated polymorphism (or disorder-non-associated polymorphism) is not critical. Numerous methods of detecting occurrence of a polymorphism are known in the art, and substantially any of those methods can be used in the kits and methods described herein. Naturally, the reagents included in the kit will vary depending on the method to be used to detect the polymorphisms. Examples of some suitable polymorphism detection methods are provided below.

In one embodiment, a pair of oligonucleotide primers are used to amplify a portion of the gene that includes a polymorphic region. Detection of one or more of the polymorphisms that occur at the polymorphic region can be achieved by contacting the amplified portion with an oligonucleotide having a sequence such that it will anneal under stringent conditions with the amplified portion only if one polymorphism occurs at the portion, but will not anneal with the amplified portion if another polymorphism occurs at that portion. Various acceptable stringent conditions are known in the art, and can be modified by the skilled artisan as appropriate to any particular amplified portion/oligonucleotide pair. An example of stringent conditions is hybridization in 6× sodium chloride/sodium citrate (SSC) at about 45° C., followed by one or more washes in 0.2×SSC, 0.1% (w/v) SDS at 50° C.

In an alternative embodiment, one or more molecular beacon oligonucleotides are used to detect polymorphisms (disorder-associated, non-disorder-associated, or both) in a sample that contains a copy of the subject's genome, a fraction of the subject's genome, or amplification products generated from the subject's genome (e.g., amplified portions of one or more of the genes disclosed herein in which polymorphisms are known to occur).

Molecular beacon probes are single-stranded oligonucleotides having a fluorescent label (e.g. rhodamine, FAM, TET, VIC, JOE, or HEX) attached at or near the 5'-end thereof and a fluorescence quencher (e.g. TAMRA or DABCYL) attached at or near the 3'-end thereof (or vice versa), as described (Kostrikis et al., 1998, Science 279:1228-1229). The sequence of each molecular beacon probe is selected to include two complementary hairpin regions, whereby the probe can self-anneal to form a hairpin structure. The 5'- and 3'-ends are brought into close association when the hairpin structure forms. The probe also comprises a targeting portion which is selected to be complementary to a target sequence (e.g. a single polymorphism of a gene disclosed herein). The targeting portion and at least one of the hairpin regions are located in close proximity to one another, meaning that the targeting portion either overlaps the hairpin region or flanks it, having no more than about 5 nucleotide residues therebetween.

If the hairpin regions of the molecular beacon probe anneal with one another, then the probe does not fluoresce, because the hairpin structure forms and the fluorescence quencher attached to one end of the probe quenches fluorescence of the label attached to the other end of the probe. If the targeting portion of the probe anneals with a region of a nucleic acid having the target sequence, then formation of the hairpin structure is inhibited, the fluorescence quencher is not brought into association with the fluorescent label, and the probe fluoresces. Multiple molecular beacon probes can be used in a single reaction mixture, and fluorescence associated with the probes can be differentiated if the molecular beacon probes are spectrally distinct.

Thus, in this embodiment, one or more molecular beacon probes are used, each having targeting portion which is complementary to a target region (e.g. 20 to 40 nucleotide residues, more preferably 20 to 30 residues) of one polymorphism of a gene disclosed herein. If the polymorphism to be detected is a single nucleotide polymorphism (SNP), then the target region includes, and preferably is approximately centered around, the nucleotide residue at which the polymorphism occurs. More preferably, two such probes are used, one having a targeting region completely complementary to the target region of one polymorphism of the gene (e.g., one of two polymorphisms of a particular SNP), and the other having a targeting region completely complementary to the target region of a corresponding polymorphism of the gene (e.g., the other polymorphism of the SNP if there are only two polymorphic forms), so that occurrence of disorder-associated and non-disorder-associated polymorphisms can be simultaneously determined.

In yet another embodiment of how polymorphisms in gene disclosed herein can be assessed, oligonucleotide primers which are complementary to a region adjacent a characteristic residue of the polymorphism are extended using a polymerase enzyme, and the identity of the nucleotide residue that is added to the primer in the position complementary to the characteristic residue is determined. The primer can be extended in the presence of non-extendable nucleotide residues in order to ensure that a limited number of nucleotide residues (or only one) are incorporated into the primer. Methods of this type are known in the art (e.g., the SNP-IT® technology of Orchid Biocomputer, Inc.) and are described, for example in U.S. Pat. Nos. 6,013,431 and 6,004,744.

Methods of Assessing Susceptibility to Individual Skin Disorders

An patient's skin health score is predictive of the patient's susceptibility to individual skin disorders (a higher score indicating a greater susceptibility to such disorders). The rate or likelihood of development and progression of skin disorders can be estimated by assessing the skin health (i.e., determining a skin health score) of a patient. The rate or likelihood of development and progression of the particular skin disorders disclosed herein can be estimated by assessing occurrence of the disorder-associated polymorphisms disclosed herein.

The individual skin disorders for which susceptibility can be assessed using these methods are not limited to those disclosed herein. The methods can be used to assess susceptibility to substantially any skin disorder. However, it is likely that congenital skin defects which lead to development of aberrant skin in utero or during the first few years of life are unlikely to be associated with the disorder-associated polymorphisms described herein.

Kits for Assessing Skin Health

The invention includes a kit for assessing the skin health of a human and/or the susceptibility of the human to a skin disorder. The kit contains reagents for performing one or more of the methods described herein. The reagents used in certain embodiments of the methods described herein are indicated above. Reagents useful for performing those methods using a variety of alternative sample preparation and polymorphism detection methods or chemistries are apparent to the skilled artisan.

Kits for detecting polymorphisms in individual genes are known in the art, and the kit of the invention can have similar components. However, a critical feature of the kit is that it includes reagents that permit its user to detect disorder-associated polymorphisms in at least two (or at least three, four, six, eight, ten, or fifteen or more) genes disclosed herein.

In one embodiment, the kit includes a plurality of oligonucleotides which anneal under stringent conditions with a disorder-associated polymorphism of one of the genes (e.g., one of the genes identified herein as being of particular relevance for skin health), but not with a non-disorder associated-polymorphism. Each of the oligonucleotides can be attached to a surface in order to facilitate handling of the oligonucleotide. The oligonucleotides can be linked with a plurality of surfaces (e.g., oligonucleotides for a particular polymorphism being attached to a particle discrete from a particle to which oligonucleotides for another polymorphism are attached), or they can be attached to discrete regions of a single surface (e.g., a glass or silicon surface having oligonucleotides attached at defined locations thereon, as in the GENECHIP™ device of Affymetrix, Inc.). Annealing between individual oligonucleotides and the polymorphism corresponding thereto can be detected using standard methods. The kit can also comprise oligonucleotides that are useful as molecular beacon probes or as extendable primers.

In one embodiment, the kit further comprises a DNA collection kit or apparatus, such as that described in co-pending U.S. Pat. No. 6,291,171. Advantageously, DNA collected using the kit or apparatus can be stored or archived, and subjected to additional testing as previously unknown disorder-associated polymorphisms are discovered in the genes disclosed herein, or as the significance of previously unappreciated polymorphisms is realized.

The invention also relates to a method of assessing the advisability that a human should consume or apply a nutritional product comprising a skin protective agent such as those described above. The method is performed as described herein for assessing the skin health of a human. If poorer skin health is detected in the human (i.e., relative to a human not having a disorder-associated polymorphism in a gene identified herein), then it is more advisable the human should consume or apply a nutritional product comprising the skin protective agent. A greater skin health score (i.e., corresponding to poorer skin health) in a human correlates with an increased advisability that the human should use such a nutritional product, and also indicates that a greater dose of the skin agent(s) should be included in the nutritional product.

It will be appreciated by those skilled in the art that changes can made to the embodiments described above without departing from the broad inventive concept thereof.

The disclosure of every patent, patent application, and publication cited herein is hereby incorporated herein by reference in its entirety.

This invention is not limited to the particular embodiments disclosed, and includes modifications within the spirit and scope of the present invention as defined by the appended claims.

What is claimed is:

1. A method of assessing skin health of a human, the method comprising detecting occurrence in the human's genome of disorder-associated polymorphisms in each of:
   mitochondrial manganese superoxide dismutase (MnSOD), wherein the disorder-associated polymorphism in mitochondrial MnSOD is selected from the group consisting of: a polymorphism manifested as occurrence of a codon encoding alanine at amino acid residue 9, a polymorphism manifested as occurrence of a codon encoding valine at amino acid residue 9, and a polymorphism manifested as occurrence of a codon encoding isoleucine at amino acid residue 58;
   cytoplasmic copper/zinc superoxide dismutase (CZSOD), wherein the disorder-associated polymorphism in cytoplasmic CZSOD is selected from the group consisting of: a polymorphism manifested as occurrence of a codon encoding valine at amino acid residue 7, a polymorphism manifested as occurrence of a codon encoding glutamic acid at amino acid residue 7, a polymorphism manifested as occurrence of a codon cysteine at amino acid residue 6, and a polymorphism manifested as occurrence of a codon encoding phenylalanine at amino acid residue 6;
   catalase, wherein the disorder-associated polymorphism in catalase is selected from the group consisting of: a polymorphism manifested as occurrence of a cytosine residue at nucleotide residue-262 and a polymorphism manifested as occurrence of a thymine residue at nucleotide residue-262; and
   human glutathione peroxidase (hGPX1), wherein the disorder-associated polymorphism in glutathione peroxidase (hGPX1) selected from the group consisting of: a polymorphism manifested as occurrence of a codon encoding proline at amino acid residue 198 of hGPX1, and a polymorphism manifested as occurrence of a codon encoding leucine at amino acid residue 198 of hGPX1; and at least one additional disorder-associated polymorphism in genes selected from the group consisting of:
   a) the gene which encodes glutathione S transferase P1 (GSTP1); wherein the polymorphism is one or more of i) a polymorphism manifested as occurrence of a codon encoding valine at amino acid residue 105 of GSTP1; and/or
ii) a polymorphism manifested as occurrence of a codon encoding isoleucine at amino acid residue 105 of GSTP 1 b) the gene which encodes NAD(P)H:quinone oxidoreductase; wherein the polymorphism is one or more of
i) a polymorphism manifested as occurrence of a cytosine residue at nucleotide residue 242 of the gene encoding NAD(P)H:quinone oxidoreductase; and/or
ii) a polymorphism manifested as occurrence of a thymine residue at nucleotide residue 242 of the gene encoding NAD(P)H:quinone oxidoreductase c) the gene which encodes epoxide hydrolase; wherein the polymorphism is one or more of
i) a polymorphism manifested as occurrence of a polymorphism manifested as occurrence of a thymine residue at nucleotide residue 113 in exon 3 of the gene which encodes epoxide hydrolase; and/or
ii) a polymorphism manifested as occurrence of a cytosine residue at nucleotide residue 113 in exon 3 of the gene which encodes epoxide hydrolase d) the gene which encodes tumor necrosis factor alpha (TNF-alpha); wherein the polymorphism is one or more of
i) a polymorphism manifested as occurrence of an adenine residue at nucleotide residue-238 of the gene which encodes TNF-alpha; and/or
ii) a polymorphism manifested as occurrence of an adenine residue at nucleotide residue-308 of the gene which encodes TNF-alpha e) the gene which encodes NADH/NADPH oxidase p22 subunit (the phox gene); wherein the polymorphism is one or more of
i) a polymorphism manifested as occurrence of a cytosine residue at nucleotide residue 242 of the phox gene; and/or
ii) a polymorphism manifested as occurrence of a thymine residue at nucleotide residue 242 of the phox gene f) the gene which encodes nitric oxide synthase; wherein the polymorphism is one or more of
i) a polymorphism manifested as occurrence of a 27 base pair nucleotide residue between nucleotide residues 5130 and 5511 of the gene encoding nitric oxide synthase; and/or
ii) a polymorphism manifested as non-occurrence of a 27 base pair nucleotide residue repeat between nucleotide residues 5130 and 5511 of the gene encoding nitric oxide synthase g) the gene which encodes cytochrome P450; and wherein the polymorphism is one or more of
i) a polymorphism manifested as occurrence of an adenine residue at nucleotide residue-290 of the gene encoding cytochrome P450; and/or
ii) a polymorphism manifested as occurrence of a guanine residue at nucleotide residue-290 of the gene encoding cytochrome P450 h) the gene which encodes matrix metalloproteinase 1 (MMP-1) wherein the polymorphism is one more of
i) a polymorphism manifested as occurrence of a single guanine residue at nucleotide residue-1607 of the human gene encoding MMP-1; and/or
ii) a polymorphism manifested as occurrence of two consecutive guanine residues at a site including nucleotide residue-1607 of the human gene encoding MMP-1; and correlating the occurrence of the polymorphisms to skin health by calculating an odds ratio that describes the likelihood that the human is susceptible to poor skin health, wherein the higher odds ratio the greater the likelihood that the human is susceptible to poor skin health.

2. The method of claim 1, wherein occurrence of polymorphisms is detected in at least four of the genes a) through h).

3. The method of claim 1, wherein occurrence of polymorphisms is detected in at least five of the genes a) through h).

4. The method of claim 1, wherein occurrence of polymorphisms is detected in at least eight of the genes a) through h).

5. The method of claim 1, wherein occurrence of polymorphisms is detected in each of the genes a) through h).

6. The method of claim 1, wherein a human whose genome comprises one or more of the polymorphisms is advised to improve nutrition or apply a skin protective agent.

7. The method of claim 1, wherein detecting the occurrence of the disorder-associated polymorphism comprises the steps of:
(a) contacting a nucleic acid derived from the human's genome with a first oligonucleotide; and
(b) annealing the first oligonucleotide and the nucleic acid, whereby annealing of the first oligonucleotide and the nucleic acid is an indication that the human's genome comprises the disorder-associated polymorphism.

8. The method of claim 7, wherein the first oligonucleotide is attached to a support.

9. The method of claim 8, wherein the support has a plurality of different first oligonucleotides attached thereto, wherein each oligonucleotide anneals with the disorder-associated polymorphism.

10. The method of claim 8, wherein the support has attached thereto at least five first oligonucleotides that anneal with the disorder-associated polymorphisms.

11. The method of claim 8, wherein the support has attached thereto at least ten first oligonucleotides that anneal with the disorder-associated polymorphisms.

12. The method of claim 8, wherein the support has attached thereto at least fifteen first oligonucleotides that anneal with the disorder-associated polymorphisms.

13. The method of claim 7, wherein the first oligonucleotide is a molecular beacon oligonucleotide.

14. The method of claim 7, wherein detecting the occurrence of the disorder-associated polymorphism further comprises the steps of:
(a) contacting the nucleic acid with a second oligonucleotide that anneals with a non-disorder-associated polymorphism; and
(b) annealing the second oligonucleotide and the nucleic acid, whereby annealing of the second oligonucleotide and the nucleic acid is an indication that the human's genome does not comprise the disorder-associated polymorphism.

15. The method of claim 14, wherein the second oligonucleotide is attached to a support.

16. The method of claim 15, wherein the first and second oligonucleotides are attached to the same support.

17. The method of claim 14, wherein the second oligonucleotide is a molecular beacon oligonucleotide.

18. The method of claim 14, wherein the first and second oligonucleotides are spectrally distinct molecular beacon oligonucleotides.

* * * * *

UNITED STATES PATENT AND TRADEMARK OFFICE
CERTIFICATE OF CORRECTION

PATENT NO. : 8,313,930 B2
APPLICATION NO. : 11/731180
DATED : November 20, 2012
INVENTOR(S) : John R. DePhillipo et al.

It is certified that error appears in the above-identified patent and that said Letters Patent is hereby corrected as shown below:

On the Title Page:

(73) Assignee: "Genelink, Inc., Margate, NY (US)" should read --Genelink, Inc., Margate, NJ (US)--

Signed and Sealed this
Eighth Day of January, 2013

David J. Kappos
*Director of the United States Patent and Trademark Office*